United States Patent [19]

Fuchs et al.

[11] B 4,014,753

[45] Mar. 29, 1977

[54] PROPYLENE OXIDE RECOVERY BY AZEOTROPIC DISTILLATION OF METHYL FORMATE-2-METHYLPENTANE

[75] Inventors: Werner Fuchs, Ludwigshafen; Rolf Platz; Norbert Rieber, both of Mannheim; Andreas Scholz, Ludwigshafen, all of Germany

[73] Assignee: Badische Anilin- & Soda-Fabrik Aktiengesellschaft, Ludwigshafen (Rhine), Germany

[22] Filed: May 21, 1973

[21] Appl. No.: 361,954

[44] Published under the second Trial Voluntary Protest Program on April 6, 1976 as document No. B 361,954.

[30] Foreign Application Priority Data

May 26, 1972 Germany .................... 2225657

[52] U.S. Cl. .................... 203/1; 203/70; 203/60; 203/91; 260/348.5 R
[51] Int. Cl.$^2$ .................... B01D 3/34
[58] Field of Search .................... 203/60, 52, 70, 91, 203/1; 260/348.5 V

[56] References Cited

UNITED STATES PATENTS

| | | | |
|---|---|---|---|
| 2,498,928 | 2/1950 | Ray | 203/60 |
| 2,622,060 | 12/1952 | Robeson | 203/37 |
| 3,258,491 | 6/1966 | Lacey et al. | 260/348.5 V |
| 3,350,415 | 10/1967 | Benning | 260/348.5 V |
| 3,350,418 | 10/1967 | Bowe et al. | 203/70 |
| 3,350,419 | 10/1967 | Null et al. | 203/70 |
| 3,449,219 | 6/1969 | Schmidt | 203/70 |
| 3,464,897 | 9/1969 | Jubin | 203/70 |
| 3,607,669 | 9/1971 | Jubin | 203/70 |
| 3,632,482 | 1/1972 | Hoory et al. | 203/70 |

FOREIGN PATENTS OR APPLICATIONS 1,150,060  6/1963  Germany .................... 260/348.5

*Primary Examiner*—Norman Yudkoff
*Assistant Examiner*—Frank Sever
*Attorney, Agent, or Firm*—Johnston, Keil, Thompson & Shurtleff

[57] ABSTRACT

Recovery of pure propylene oxide from propylene oxide which is contaminated by $C_6$ hydrocarbons and methyl formate, by distillation with the addition of more methyl formate so that the amount of methyl formate is four times that of the 2-methylpentane present.

5 Claims, No Drawings

PROPYLENE OXIDE RECOVERY BY AZEOTROPIC DISTILLATION OF METHYL FORMATE-2-METHYLPENTANE

The invention relates to a process for the recovery of pure propylene oxide from a mixture containing propylene oxide by a single fractional distillation in the presence of an agent which forms an azeotrope with the impurities.

The production of propylene oxide (1,2-propylene oxide) by oxidation of propylene in liquid phase with oxygen or air has been described many times. Depending on the method, a large number of byproducts are formed and have to be separated from the propylene oxide. This separation is particularly difficult in the case of compounds which are very similar to propylene oxide in boiling behavior (for example methyl formate) or which form azeotropes with propylene oxide (such as 2-methylpentane).

Several methods are already known for the purification of propylene oxide. Thus for example an extractive distillation with higher hydrocarbons as extractants is proposed for the separation of $C_6$ hydrocarbons in U.S. Pat. No. 3,464,897. Similarly an extractive distillation with hydrocarbons is recommended in German Patent 1,224,293 and U.S. Pat. No. 3,338,800 for the separation of methyl formate.

$C_6$ hydrocarbons, aldehydes and methyl formate may furthermore be separated by an extractive distillation with aqueous alkaline liquor in two stages. Other methods for the separation of methyl formate are based on the alkaline hydroylsis of the ester or on azeotropic distillation of the methyl formate with n-pentane (cf. U.S. Pat. Nos. 2,550,847, 2,622,060 and 3,071,601).

It is an object of the invention to provide a simple process which uses a crude propylene oxide containing varying amounts of 2-methylpentane, methyl formate and acetaldehyde without adding any substance other than those already present and which may cause further contamination.

The invention is based on the observation that 2-methylpentane forms an azeotrope not only with propylene oxide but also with methyl formate, the azeotrope having a lower boiling point than the individual components.

We have found that propylene oxide can be recovered advantageously by distillation from a liquid mixture containing varying amounts of acetaldehyde, methyl formate and 2-methylpentane where there are at least 4 parts by weight of methyl formate to each 1 part by weight of 2-methylpentane by feeding the crude mixture to the middle portion of a distillation column and withdrawing propylene oxide at the base of the column.

Specifically the process of the invention may conveniently be carried out as follows: crude propylene oxide (which has been obtained for example by direct oxidation of propylene with oxygen in liquid phase and which generally contains from 60 to 99% of propylene oxide, 1 to 10% of acetaldehyde, 1 to 25% of methyl formate and 0.1 to 3% of 2-methylpentane in addition to minor amounts of other low boiling point impurities) is if necessary provided with more methyl formate and is continuously supplied at a point above the middle to a distillation column having from 120 to 250 actual trays and an evaporator. The distance of the feed point from the end of the column may conveniently be at least 50 to 75 trays. Depending on the reflux ratio (which may be for example from 50 to 200, reflux ratio being defined as the volumetric ratio of condensate reflux to condensate discharge) the said number of trays represents a theoretical number of about 180 to 200 for the whole column and about 30 to 60 for the length of the stripping and rectifying section of the column.

The feed point is generally at from 50 to 60% of the height of the column or the corresponding number of trays. The temperature at the feed point is advantageously about 50°C at a pressure of 2 bar (1 bar equals 0.987 atm.). The process may generally be carried out well at a pressure of from 0.5 to 5 bar, a temperature of from about 20° to 60°C at the feed point then being recommended.

Acetaldehyde, methyl formate, 2-methylpentane and small amounts of the propylene oxide supplied are withdrawn overhead, liquefied in a condenser and collected in a container. Some of the condensate is returned to the column as reflux as described. The bottoms product consists of propylene oxide having a purity of more than 99.9%. Propylene oxide may also be withdrawn as gas above the bottoms or the propylene oxide collected in the bottom is again distilled when the requirement as to purity is high.

When the crude propylene oxide used does not contain the necessary 4 parts by weight of methyl formate per part by weight of 2-methylpentane, or if the proportion of methyl formate varies, the amount of methyl formate to be added may be taken from a reservoir obtained independently. The proportion of 2-methylpentane is determined by one of the conventional methods, for example by an appropriate process gas chromatograph which may then control the metering of the methyl formate.

Purification of propylene oxide according to the invention may naturally be carried out batchwise. The process described above will then be modified according to generally known rules.

Distillation columns of conventional design, for example bubble tray columns or valve plate columns may be used as columns; packed columns may also be used.

The following Examples illustrate the invention.

EXAMPLE 1

The crude propylene oxide to be purified contains the following impurities:
6% of acetaldehyde;
6% of methyl formate; and
1% of 2-methylpentane.

250 g per hour of crude propylene oxide is supplied to the 100th tray of a column with 180 bubble trays, a height of 13 meters and a diameter of 5 centimeters which is operated at 2 bar. The reflux ratio is 70 and the overhead temperature is about 44°C. 35 g per hour of distillate is obtained which has approximately the following composition:
43% of acetaldehyde;
43% of methyl formate;
7% of 2-methylpentane; and
7% of propylene oxide.

The bottoms product is withdrawn at an evaporator temperature of 66°C. The propylene oxide thus obtained contains 5 ppm of methyl formate, 5 ppm of acetaldehyde and 3 ppm of 2-methylpentane.

EXAMPLE 2

The crude propylene oxide to be purified contains the following impurities:
  8% of acetaldehyde;
  25% of methyl formate; and
  0.2% of 2-methylpentane.

A packed column having about 110 theoretical trays, a height of 4 meters and a diameter of 32 millimeters is used which is operated at 1 bar and with a reflux ratio of 100. About 40 grams per hour of the mixture is supplied at 30°C at 55% of the height of the column. About 15 grams per hour of distillate is taken overhead; it has about the following composition:
  67% of methyl formate;
  21% of acetaldehyde;
  11% of propylene oxide; and
  0.5% of 2-methylpentane.

The bottoms of the column, which is kept at about 39°C, has propylene oxide containing 5 ppm of acetaldehyde, 7 ppm of methyl formate and 2 ppm of 2-methylpentane withdrawn from it.

EXAMPLE 3

The crude propylene oxide to be purified contains the following impurities:
  10% of methyl formate;
  7% of acetaldehyde; and
  0.1% of 2-methylpentane.

The impurities are in a batch operated packed column having about 135 theoretical trays, a height of 4.5 meters and a diameter of 30 millimeters at 1 bar pressure and a reflux ratio of 60. The propylene oxide remaining in the bottoms contains the said impurities in concentrations of less than 10 ppm.

We claim:

1. A process for the recovery of propylene oxide from a liquid mixture containing from 60 to 99% of propylene oxide, up to 10% of acetaldehyde, up to 25% of methyl formate and up to 3% of 2-methylpentane in addition to minor amounts of other low-boiling impurities by distillation, wherein
   a. the relative amounts of methyl formate and 2-methylpentane in the liquid mixture are determined,
   b. the methyl formate content is corrected in such a way as to give a ratio of at least 4 parts by weight of methyl formate to each part by weight of 2-methylpentane,
   c. the mixture is supplied to the feed point of a column having from 100 to 200 theoretical trays, which feed point is spaced by from 30 to 60 theoretical trays from the ends of the column, and
   d. propylene oxide is recovered at the bottom of said column.

2. A process as set forth in claim 1 wherein the mixture is supplied to the column at a temperature of from 20° to 60°C.

3. A process as set forth in claim 1 wherein the distillation is carried out at a pressure of from 0.5 to 5 bar.

4. A process as set forth in claim 1 wherein a reflux ratio of from 10 to 200 is maintained.

5. A process as set forth in claim 1 wherein said liquid mixture contains from 60 to 99% of propylene oxide, 1 to 10% of acetaldehyde, 1 to 25% of methyl formate and 0.1 to 3% of 2-methylpentane.

* * * * *